United States Patent [19]

Ragan

[11] Patent Number: 6,147,214

[45] Date of Patent: Nov. 14, 2000

[54] PROCESS AND INTERMEDIATES FOR THE PREPARATION OF 4'-TRIFLUOROMETHYL-BIPHENYL-2-CARBOXYLIC ACID (1,2,3,4-TETRAHYDRO-ISOQUINOLIN-6-YL)-AMIDE

[75] Inventor: John Anthony Ragan, Gales Ferry, Conn.

[73] Assignee: Pfizer Inc, New York, N.Y.

[21] Appl. No.: 09/403,266

[22] PCT Filed: Apr. 6, 1998

[86] PCT No.: PCT/IB98/00493

§ 371 Date: Oct. 15, 1999

§ 102(e) Date: Oct. 15, 1999

[87] PCT Pub. No.: WO98/47875

PCT Pub. Date: Oct. 29, 1998

Related U.S. Application Data

[60] Provisional application No. 60/044,690, Apr. 18, 1997.

[51] Int. Cl.$^7$ .......................... C07D 217/04; C07C 233/80
[52] U.S. Cl. ............................................. 546/143; 564/184
[58] Field of Search ............................. 546/143; 564/184

[56] References Cited

FOREIGN PATENT DOCUMENTS 9640640  12/1996  WIPO .

OTHER PUBLICATIONS

O. Orazi et al., *J. Chem. Soc. Perkin Trans.* 1, 1986, 1977–1982.
G. Stokker, *Tetrahedron Lett.* 1996, 5453–5456.
K. Isobeb et al., *Chem. Pharm Bull.* 1998, 1275–1282. Selective Cleavage of Aromatic Rings by Ozonolysis. I. Application to o–Dimethoxybenzene Derivatives.
F. Kuffner et al., Monatshefte Fur Chemie., col. 91, 1960, Wein at pp. 1152–1161, XP002070019 see p. 1160, Über die Konstitution eines Nebenalkaloides aus Adhatoda vasica Nees.
A. Pictet et al., Bericate der Deutschen Chemischen Gesell-schgft (1911) 44, pp. 2030–2036. Search Report for PCT/IB98/00493.
March J. Advanced Organic Chemistry. Second Edition. pp. 854, 1125, 1977.

*Primary Examiner*—Evelyn Mei Huang
*Attorney, Agent, or Firm*—Peter C. Richardson; Paul H. Ginsburg; Seth H. Jacobs

[57] ABSTRACT

An improved process, and intermediates, for the preparation of 4'-trifluoromethyl-biphenyl-2-carboxylic acid (1,2,3,4-tetrahydro-isoquinoline-6-yl) amide (I), are disclosed. Compound (I) is useful as an inhibitor of microsomal triglyceride transfer protein and/or apolipoprotein B secretion, and which are accordingly useful for the preparation and treatment of atherosclerosis and its clinical sequelae, for lowering serum lipids, and related diseases.

10 Claims, No Drawings

PROCESS AND INTERMEDIATES FOR THE PREPARATION OF 4'-TRIFLUOROMETHYL-BIPHENYL-2-CARBOXYLIC ACID (1,2,3,4-TETRAHYDRO-ISOQUINOLIN-6-YL)-AMIDE

This application is the national phase of PCT/IB 98/00493, filed Apr. 6, 1998, which claims the benefit of priority of U.S. provisional application Ser. No. 60/044,690, filed Apr. 18, 1997.

FIELD OF THE INVENTION

This invention relates to an improved process and intermediates useful in the preparation of 4'-trifluoromethyl-biphenyl-2-carboxylic acid (1,2,3,4-tetrahydro-isoquinolin-6-yl)-amide (I), below. Compound I is useful in the preparation of 4'-trifluoromethyl-biphenyl-2-carboxylic acid [2-(1H-[1,2,4-triazol-3-ylmethyl)]-(1,2,3,4-tetrahydro-isoquinolin-6-yl)-amide whose formula is

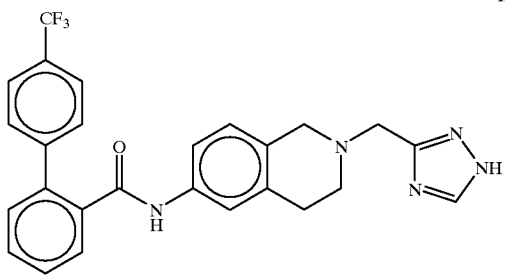

II

Compound II is useful as an inhibitor of microsomal triglyceride transfer protein and/or apolipoprotein B (Apo B) secretion, and which are accordingly useful for the prevention and treatment of atherosclerosis and its clinical sequelae, for lowering serum lipids, and related diseases.

BACKGROUND OF THE INVENTION

Microsomal triglyceride transfer protein (MTP) catalyzes the transport of triglyceride, cholesteryl ester, and phospholipids. It has been implicated as a probable agent in the assembly of Apo B-containing lipoproteins, biomolecules which contribute to the formation of atherosclerotic lesions. See European Patent application publication no. 0 643 057 A1, European Patent application publication no. 0 584 446 A2, and Wetterau et al., Science, 258, 999–1001, (1992). Compounds which inhibit MTP and/or otherwise inhibit Apo B secretion are accordingly useful in the treatment of atherosclerosis. Such compounds are also useful in the treatment of other diseases or conditions in which, by inhibiting MTP and/or Apo B secretion, serum cholesterol and triglyceride levels can be reduced. Such conditions include hypercholesterolemia, hypertriglyceridemia, pancreatitis, and obesity; and hypercholesterolemia, hypertriglyceridemia, and hyperiipidemia associated with pancreatitis, obesity, and diabetes.

PCT application serial no. PCT/IB95/00448 (hereafter "the '448 application") and U.S. Patent Application Serial No. 60/032307 (hereafter "the '307 application"), assigned to the Assignee of this application and incorporated herein in their entirety, describe methods for the preparation of compound I and its conversion to compound II. All other documents referred to herein are also incorporated herein in their entirety.

SUMMARY OF THE INVENTION

According to one embodiment of the invention there is provided an improved process for the preparation of the compound of the formula

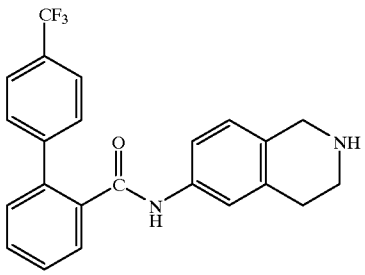

I which comprises treating the compound of formula

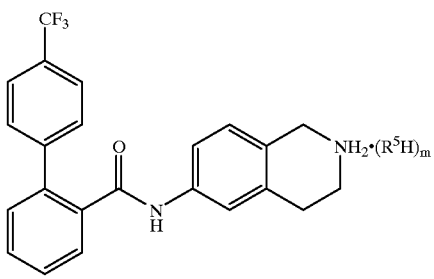

III m is 0 or 1 and $R^5H$ is a first acid, with a source of formaldehyde, such as formalin, paraformaldehyde and trioxane, in the presence of a second acid, wherein said first and second acids may be the same or different and are selected from mineral acids such as hydrochloric, sulfuric, nitric and phosphoric, organic acids such as sulfonic acids, e.g. benzenesulfonic (besylic), p-toluenesulfonic (PTSA, tosylic), methanesulfonic (MSA, mesylic) and trifluoromethanesulfonic (triflic); carboxylic acids e.g., formic, acetic, proprionic, benzoic, citric, tartaric, maleic, fumaric, succinic and malic. Preferably the source of formaldehyde is paraformaldehyde, the first acid is HCl or formic acid and the second acid is formic acid.

According to another aspect of the above embodiment there is provided a process wherein the compound of formula III, wherein m is 1, is prepared by treating the compound of the formula

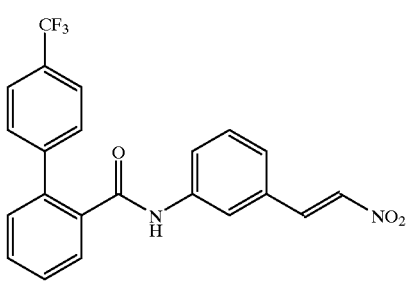

IV in an inert medium, containing a first acid, with a reducing agent selected from hydrogen in the presence of a hydrogenation catalyst such as Raney Ni, Pd/C and Pd(OH)$_2$; and aluminum hydrides; and borane; and borohydrides. The compound (group) of the formula III, wherein m is 0 is prepared therefrom by neutralization of the the $R^5H$.

Another aspect of the above embodiment provides a process wherein the compound of formula IV is prepared by treating the compound of the formula V

V

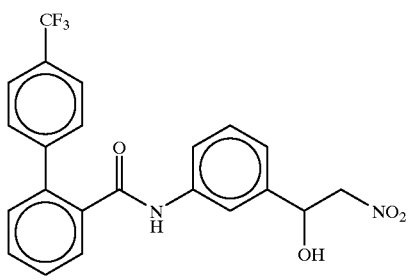

with a dehydrating agent, selected from $(C_1-C_6)$alkyl or $(C_6-C_{10})$aryl sulfonyl or carbonyl halide or anhydride, in the presence of a base. A preferred dehydrating agent is mesyl chloride.

Yet another aspect of the above embodiment provides a process wherein the compound of formula V is prepared by treating the compound of the formula VI

VI

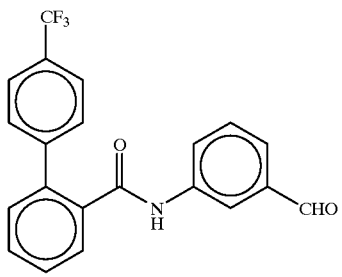

with nitromethane in the presence of a base.

According to another aspect of the above embodiment there is provided a process wherein the compound of formula VI is prepared by treating the compound of the formula VII

VII

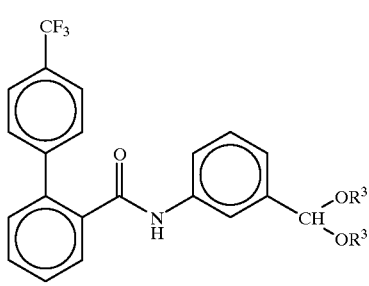

each $R^3$ is, independently, selected from $(C_1-C_6)$alkyl or both $R^3$s together form a group of the formula

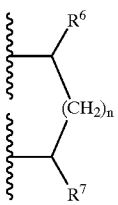

wherein n is 0 or 1, and $R^6$ and $R^7$ are each selected from H and $(C_1-C_2)$alkyl or $R^6$ and $R^7$ together with the carbons to which they are attached form a $(C_3-C_8)$cycloalkyl or $(C_6-C_{10})$aryl ring, with an aqueous acid.

Another aspect of the above embodiment provides a process wherein the compound of formula VII is prepared by treating the compound of the formula

IX

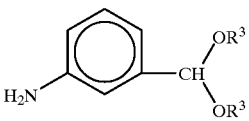

wherein $R^3$ is as defined above, with the compound of the formula

VIII

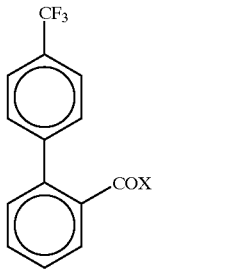

wherein X is any of the leaving groups known for the acylation of amines, such as halo, e.g., F and Cl, and $(C_2-C_6)$acyloxy, e.g., acetoxy; and $(C_6-C_{10})$aroyloxy, e.g., benzoyloxy; and $(C_6-C_{10})$aryloxy groups such as p-NO$_2$— and p-fluorophenyloxy. Preferably, X is chloro.

This embodiment further provides a process wherein the compound of formula IX is prepared by treating the compound of the formula

X

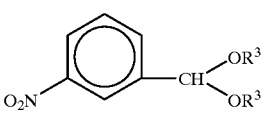

wherein $R^3$ is, as described above, with hydrogen in the presence of a hydrogenation catalyst.

According to another aspect of the above embodiment there is provided a process wherein the compound of formula XI

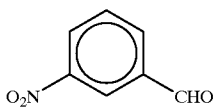

is reacted with a compound of the formula $R^3OH$, wherein $R^3$ is $(C_1-C_6)$alkyl, or a compound of the formula

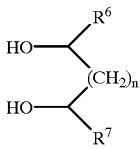

wherein n is 0 or 1, each of $R^6$ and $R^7$ is selected from H and $(C_1-C_3)$alkyl or $R^6$ and $R^7$ together with the carbons to which they are attached form a $(C_3-C_{10})$cycloalkyl or $(C_6-C_{10})$aryl ring, in the presence of a first acid, such as a cation exchange resin in its H⁺ form or an aqueous mineral acid to form the the compound of the formula X.

According to a second embodiment of the invention there is provided a compound of formula

A—CHR¹R² wherein

A is a group of the formula

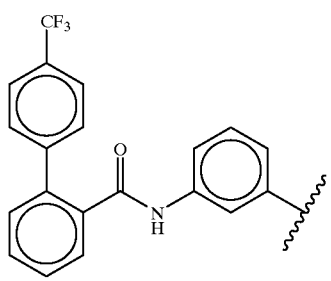

and $R^1$ is selected from H and $OR^3$ wherein $R^3$ is hydrogen or $(C_1-C_6)$alkyl, $R^2$ is selected from $OR^3$, —$CH_2$—$NH_2$ or —$CH_2$—$NO_2$; or $R^1$ and $R^2$ together form an =O or =CH—$NO_2$ group; with the proviso that when $R^1$ and $R^2$ are each an $OR^3$ group then both $R^3$s are $(C_1-C_6)$alkyl groups and the same.

According to another aspect of the above embodiment the invention provides acid addition salts of the compound of the formula

A—CHR¹R².R⁵H wherein A and $R^1$ are as defined above, $R^2$—$CH_2$—$NH_2$ and $R^5H$ is an acid selected from mineral acids such as hydrochloric, sulfuric, nitric and phosphoric, organic acids such as sulfonic acids, e.g. benzenesulfonic (besylic), p-toluenesulfonic (PTSA, tosylic), methanesulfonic (MSA, mesylic) and trifluoromethanesulfonic (triflic); carboxylic acids e.g., formic, acetic, proprionic, benzoic, citric, tartaric, maleic, fumaric, succinic and malic.

Some compounds may exhibit polymorphism. It is to be understood that the present invention encompasses any polymorphic forms, or mixtures thereof.

DETAILED DESCRIPTION

In the discussion which follows, common chemical abbreviations and acronyms have been employed: Me (methyl); Et (ethyl); THF (tetrahydrofuran); BOC (tert-butyloxycarbonyl, a blocking group); Ms (methanesulfonyl, mesyl); TFA (trifluoroacetic acid); Ac (Acetyl); RP (reverse phase); HPLC (high performance liquid chromatography);

Except where otherwise stated, R, $R^1$, $R^2$, $R^3$ and $R^4$, and formulae I and III through XI, in the reaction schemes and discussion that follow are defined as above.

SCHEME 1

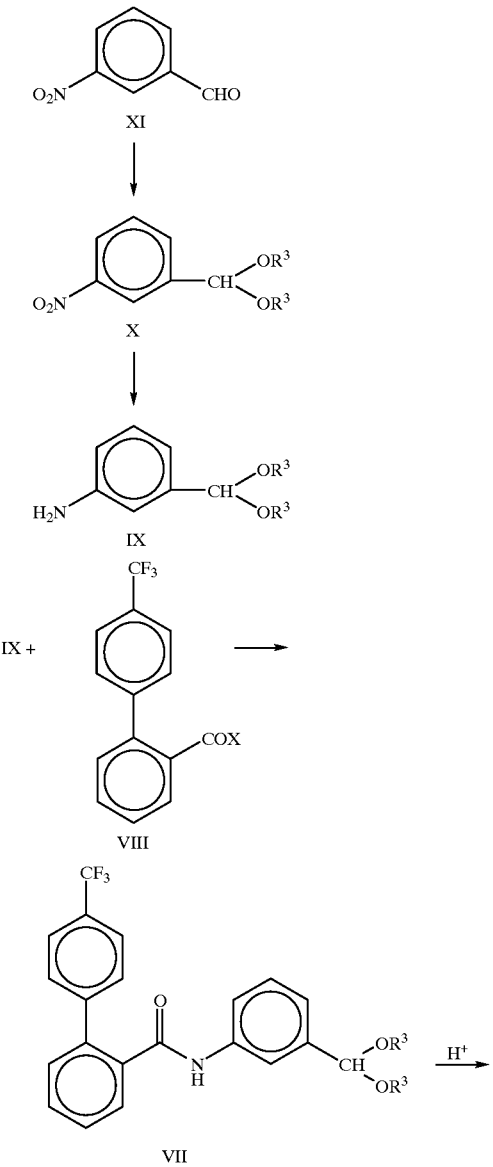

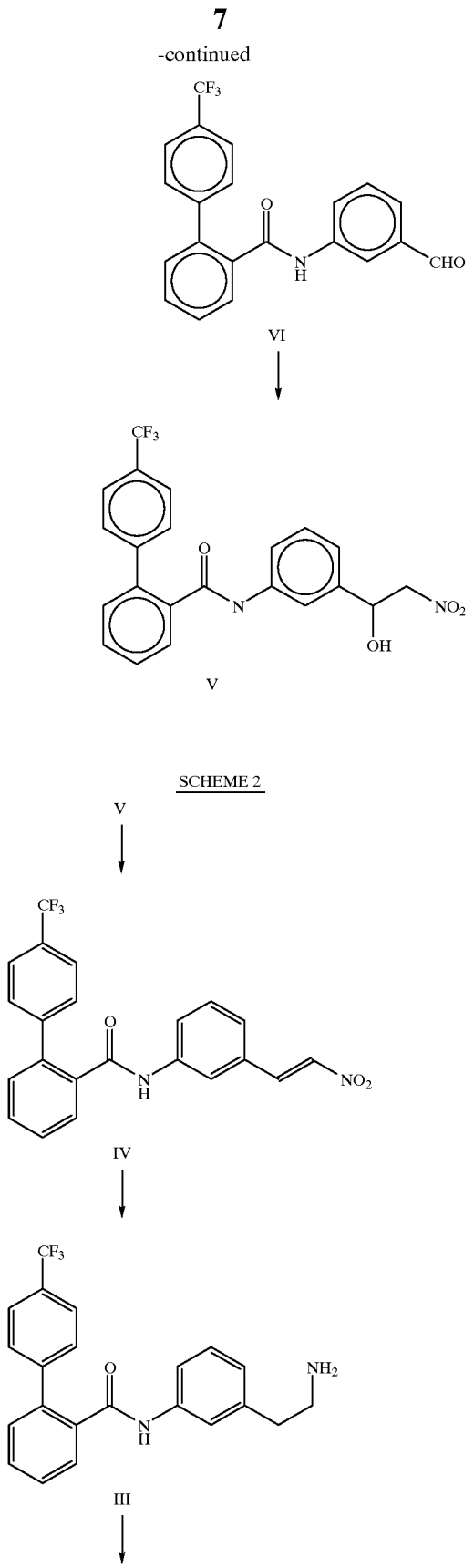

SCHEME 2

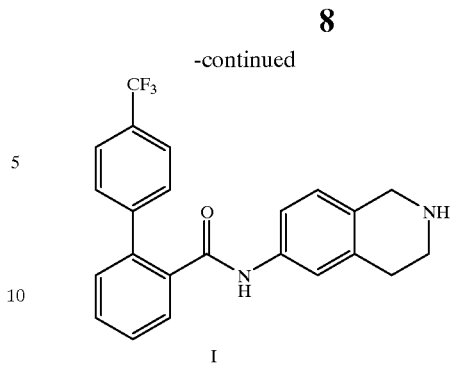

I

As shown in Scheme 1 commercially available 3-nitrobenzaldehyde XI is reacted with a compound of the formula $R^3OH$, wherein $R^3$ is $(C_1-C_6)$alkyl, or a compound of the formula

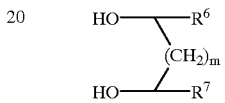

wherein n is 0 or 1, each of $R^6$ and $R^7$ is selected from H and $(C_1-C_3)$alkyl or $R^6$ and $R^7$ together with the carbons to which they are attached form a $(C_3-C_{10})$cycloalkyl or $(C_6-C_{10})$aryl ring, in the presence of a first acid, such as a cation exchange resin in its $H^+$ form or an aqueous mineral acid to form the acetal X. Acetal X is then hydrogenated to form the amino acetal IX which is subsequently treated with the compound of the formula VIII, wherein X is a "leaving" group for acylation of amines, in the presence of a base to form the acetal amide VII. Leaving groups for acylation of amines are well known in the art and include halo, such as F and Cl, and acyloxy, such as acetoxy, and aroyloxy, such as benzoyloxy, and aryloxy, such as p-$NO_2$ and p-fluorophenyloxy. Preferably X is halo and, most preferably, X is chloro. Acetal amide VII is then treated with an acid to form compound VI. Acids useful in this step include the first and second acids described above.

Acids useful in the preparation of acetal X include mineral and sulfonic acids and cation exchange resins in their $H^+$ forms. Most preferred acids are $H^+$ cation exchange resins such as the Dowex ® cation exchange resins.

Hydrogenation of X may be effected by any known method including treatment with hydrogen gas in the presence of a hydrogenation catalyst such as Pd/C, Pd(OH)$_2$/C and Raney nickel. A preferred catalyst is Pd/C and the hydrogen pressure is from about 100 to about 510 kPA (about 14–74 PSI). The preferred hydrogen pressure is about 200 to 300 kPa (about 27 to 44 PSI).

Bases useful in the conversion of X to VII are selected from the group consisting of inorganic bases such as alkali or alkaline earth hydroxides, carbonates and bicarbonates and organic bases such as tri($C_1-C_6$)alkyl amines, pyridine and morpholine. The preferred base is TEA and the preferred solvent is THF.

VII is converted to VI by any aqueous acid which is known in the art for hydrolysing acetals including cation exchange resins (in their $H^+$ form), mineral acids such as hydrochloric, sulfuric, nitric and phosphoric, and organic acids such as sulfonic acids, e.g. benzenesulfonic (besylic), p-toluenesulfonic (PTSA, tosylic), methanesulfonic (MSA, mesylic) and trifluoromethanesulfonic (triflic); and alkyl and aryl carboxylic acids e.g., acetic, proprionic, benzoic, citric, tartaric, maleic, fumaric, succinic and malic. A preferred acid for use in this step is HCl (aq).

Compound V is prepared by treating compound VI with nitromethane in the presence of a first base. Compound V, as illustrated in Scheme 2 is then treated, in an inert solvent, with a dehydrating agent selected from $(C_1-C_6)$alkyl or $(C_6-C_{10})$aryl sulfonyl or carbonyl halide or anhydride, in the presence of a second base to form compound IV. A A preferred dehydrating agent is mesyl chloride and inert solvents include chlorinated hydrocarbons, e.g., $CH_2Cl_2$. The first and second bases may be selected from those bases described above with respect to the conversion of IX to VII and may be the same or different. Preferred bases are the alkali metal carbonates and bicarbonates, preferably $Na_2CO_3$.

Compound III is prepared by reduction of compound IV. A preferred reducing agent is hydrogen, at a pressure of about 135 to 555 kPA (about 20 to 80 PSI), in the presence of a hydrogenation catalyst such as Pd/C, Pd(OH)$_2$/C, Raney nickel, and Pt/C. Other useful reducing agents are aluminum hydrides, borane, and borohydrides. The hydrogenation is effected in an inert solvent such as a $(C_1-C_6)$alkanol, e.g., ethanol, or an ester, e.g., ethyl acetate, in the presence of an acid, such as mineral acids such as hydrochloric, sulfuric, nitric and phosphoric, organic acids such as sulfonic acids, e.g. benzenesulfonic (besylic), p-toluenesulfonic (PTSA, tosylic), methanesulfonic (MSA, mesylic) and trifluoromethanesulfonic (triflic); carboxylic acids e.g., formic, acetic, proprionic, benzoic, citric, tartaric, maleic, fumaric, succinic and malic to yield the acid addition salt of compound III which can be used, directly, in the next step or after conversion to the free base. The preferred acids are HCl and formic. The reduction is preferably effected using a hydrogen pressure is about 345 kPa (50 PSI) over Pd/C in ethanol containing conc. HCl. Compound Ill is then converted to compound I by treatment with a source of formaldehyde, such as formalin, paraformaldehyde and trioxane and a $(C_1-C_6)$alkanoic acid such as formic acid at a temperature from about 25 to about 100° C. Preferably, the reaction is effected using the free base form of compound III and paraformaldehyde in formic acid at a temperature of about 60° C.

The conversion of compound I to compound II is described in copending applications Attorney Docket Nos. PC9182 and PC9687, assigned to the assignee of this application, incorporated herein in their entirety.)

Conventional methods and/or techniques of purification and separation known to those skilled in the art can be used to isolate the compounds of this invention. Such techniques include all types of chromatography (HPLC, column chromatography using common adsorbents such as silica gel, and thin layer chromatography), recrystallization, and differential (i.e., liquid—liquid) extraction techniques.

Compound II, (hereafter "the active compound"), is orally administrable and is, accordingly, used in combination with a pharmaceutically acceptable carrier or diluent suitable to oral dosage forms. Suitable pharmaceutically-acceptable carriers include inert solid fillers or diluents and sterile aqueous or organic solutions. The active compound will be present in such pharmaceutical compositions in amounts sufficient to provide the desired dosage amount in the range described below. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The active compound may also be administered parenterally. For parenteral administration the compound can be combined with sterile aqueous or organic media to form injectable solutions or suspensions. Solutions or suspensions of the active compound can be prepared in water suitably mixed with a surfactant such as hydroxypropylcellulose. Dispersions can also be prepared in sesame or peanut oil, ethanol, water, polyol (e.g., glycerol, propylene glycol and liquid polyethylene glycol) and suitable mixtures thereof; vegetable oils; N-methyl glucamine; polyvinylpyrrolidone and mixtures thereof in oils as well as aqueous solutions of water-soluble pharmaceutically acceptable salts of the compound. Under ordinary conditions of storage and use, these preparations contain a preservative to prevent the growth of microorganisms. The injectable solutions prepared in this manner can then be administered intravenously, intraperitoneally, subcutaneously, or intramuscularly.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi.

The dose of the active compound which is administered will generally be varied according to principles well known in the art taking into account the severity of the condition being treated and the route of administration. In general, the active compound will be administered to a warm blooded animal (such as a human) so that an effective dose, usually a daily dose administered in unitary or divided portions, is received, for example a dose in the range of about 0.1 to about 15 mg/kg body weight, preferably about 1 to about 5 mg/kg body weight. The total daily dose received will generally be between 1 and 1000 mg, preferably between 5 and 350 mg.

The active compound may be used in conjunction with other pharmaceutical agents, including other lipid lowering agents. Such agents include cholesterol biosynthesis inhibitors, especially HMG CoA reductase inhibitors and squalene synthetase inhibitors; bile acid sequestrants; fibrates; cholesterol absorption inhibitors; and niacin.

The present invention is illustrated by the following Examples. However, it should be understood that the invention is not limited to the specific details of these examples.

EXAMPLE 1

4'-Trifluormethyl-biphenyl-2-carboxylic acid(3-formyl-phenyl)amide

A 250 mL round bottom flask was charged with 3-nitrobenzaldehyde (5.20 g, 34.4 mmol), 100 mL methanol, and Dowex® sulfonic acid resin (e.g., Dowex 50WX4-400, Aldrich catalogue number 21-784-4) in its H$^+$ form (0.57 g), washed with two 5 mL portions of methanol and added as a slurry in 5 mL of methanol. The resulting slurry was heated at reflux for 90 minutes, then stirred overnight at ambient temperature ($^1$H NMR analysis of an aliquot showed a 95:5 ratio of the dimethyl acetal to starting aldehyde). The resin was removed by filtration, and the filtrate concentrated to a pale yellow oil. The acetal was dissolved in 100 mL THF and 10% Pd/C was added (0.52 g). The mixture was placed in a Parr® hydrogenator under 276 kPa (40 psi) hydrogen pressure). After 90 minutes, and three recharges of hydrogen, the pressure of hydrogen held steady and the reaction vessel mixture was purged with nitrogen. The catalyst was removed by filtration through Celite®, and rinsed with four 50 mL portions of THF. The filtrate was treated with triethylamine (10.6 mL, 76 mmol) followed by 4'-trifluoromethyl-biphenyl-2-carboxylic acid chloride (9.8 g, 34 mmol) added, as a solution in 10 mL THF, dropwise over 15 minutes. The resulting slurry was stirred for 20 hours at ambient temperature. 1 N HCl (aqueous) (100 mL) was then added and the mixture was stirred vigorously for 2 hours. The bulk of the THF was then removed on a rotary evaporator. The aqueous layer was extracted with three 50 mL portions of isopropyl ether/ethyl acetate (3:1 v/v). The combined organic extracts were washed twice with 1 N HCl [aq], two times with saturated aqueous NaHCO$_3$ and once with brine, and then dried over MgSO$_4$, filtered, and concentrated to give a white solid. Recrystallization from 4:1 hexanes ethyl acetate (250 mL) provided the title product as a powdery, white solid (10.5 g, 83% yield). $^1$H NMR: (CDCl$_3$): δ 9.92 (s, 1H), 7.76 (d, J=7.5 Hz, 1H), 7.69–7.67 (m, 3H), 7.62–7.52 (m, 5H), 7.46–7.42 (m, 3H), 7.06 (br s, 1H). MS (electron impact): 369 (M+, 20), 249 (100).

EXAMPLE 2

4'-Trifluoromethyl-biphenyl-2-carboxylic acid[3-(2-nitro-vinyl)-phenyl]amide

To the title product of Example 1 (3.0 g, 8.1 mmol), in 50% aqueous ethanol(15 mL), was added nitromethane (1.8 mL, 32 mmol) and Na$_2$CO$_3$ (86 mg, 0.81 mmol). The resulting solution was stirred at ambient temperature for 4 hours, and then concentrated on a rotary evaporator. The resulting product was partitioned between ethyl acetate and water (ca. 25 mL each). The organic layer was separated, dried over MgSO$_4$, filtered, and concentrated to provide the intermediate nitro alcohol as a brown oil (3.73 g).

The crude nitro alcohol (3.4 g 7.9 mmol) was dissolved in CH$_2$Cl$_2$ (90 mL), cooled to 0° C., and treated with methanesulfonyl chloride (1.5 mL, 19 mmol). After 30 minutes at 0° C., TLC analysis (10% methanol-CH$_2$Cl$_2$) indicated complete conversion to a less polar product. The solution was then washed with 1 N HCl [aq], dried over MgSO$_4$, filtered, and concentrated to give a pale yellow solid (3.3 g). Purification by silica gel chromatography (100 g silica gel, elution with 3% methanol-CH$_2$Cl$_2$) provided the title product as a colorless solid (3.2 g, 98% yield).

$^1$H NMR: (CDCl$_3$): δ 7.89 (d, J=13.9 Hz, 1H), 7.79 (d, J=7.5 Hz, 1H), 7.66–7.43 9 (m, 11H), 7.29 (d, J=7.7 Hz, 1H), 7.07 (br s, 1H). MS (chemical ionization): 413 (M+H, 100).

EXAMPLE 3

4'-Trifluoromethyl-biphenyl-2-carboxylic acid[3-(2-aminoethyl)-phenyl]amide hydrochloride A Parr® hydrogenation flask was charged with the title product of Example 2 (1.90 g, 4.61 mmol), 10% Pd/C (0.58 g), 95% ethanol (20 mL), and conc. HCl (0.96 mL, 12 mmol). The mixture was hydrogenated, under hydrogen at 276 kPa (40 psi), for 19 hours. The catalyst was removed by filtration through Celite®, and the filtrate was concentrated to provide an oily, yellow-white solid, which was 85% pure by HPLC analysis. A portion of this material was purified as its free base (i.e., the HCl salt was dissolved in methanol, treated with one molar equivalent of K$_2$CO$_3$ filtered and concentrated) by silica gel chromatography, eluting with 500:50:1 CH$_2$Cl$_2$-methanol-NH$_4$OH, providing the title product as a white solid which was homogenous by HPLC analysis.

$^1$H NMR (CDCl$_3$): δ 7.64–7.61 (m, 4H), 7.50–7.47 (m, 2H), 7.41–7.34 (m, 2H), 7.13 (br s, 1H), 7.09–7.05 (m, 1H), 6.99 (d, J=8.1 Hz, 1H), 6.84 (d, J=7.5 Hz, 1H), 4.78 (br s, 2H), 2.97 (t, J=7.3 Hz, 2H), 2.80 (t, J=7.3 Hz, 2H).

MS (chemical ionization): 385 (M=H, 100).

EXAMPLE 4

4'-Trifluoromethyl-biphenyl-2-carboxylic acid (1,2,3,4,-tetrahydroisoguinolin-6-yl)amide A 25 mL round bottom flask was charged with the free base form of the title product of Example 3 (512 mg, 1.33 mmol), paraformaldehyde (41 mg, 1.35 mmol) and formic acid (7 mL.) The resulting slurry was warmed in a 60° C. oil bath for 17 hours. After cooling to ambient temperature the slurry was neutralized by dropwise addition to a mixture of ice and saturated [aq] NH$_4$OH (12 ml, 190 mmol). The resulting solution was extracted with four portions of CH$_2$Cl$_2$. The organic extracts were combined, washed with brine, dried over K$_2$CO$_3$, filtered, and concentrated to provide 441 mg (84% of theoretical) of the title product as an off-white solid. $^1$H NMR and MS analysis of this material showed it to be identical to that prepared by the route described in the '307 and '448 applications referred to above.

What is claimed is:

1. A process for preparing the compound of the formula

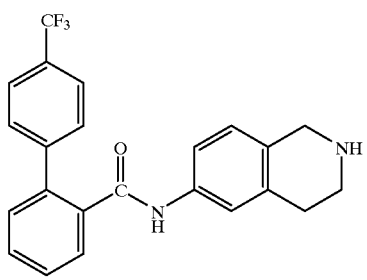

I which comprises treating the compound of formula

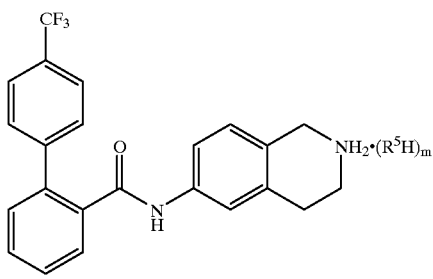
III wherein m is 0 or 1 and $R^5H$ is a first acid, with a source of formaldehyde in the presence of a second acid, wherein said first and second acid may be the same or different, and are selected from mineral acids selected from hydrochloric, sulfuric, nitric and phosphoric acid; organic acids selected from sulfonic acids which are selected from benzenesulfonic (besylic), p-toluenesulfonic (PTSA tosylic), methanesulfonic (MSA, mesylic) and trifluoromethanesulfonic (triflic) acid; and carboxylic acids which are selected from formic, acetic, propionic, benzoic, citric, tartaric, maleic, fumaric, succinic and malic acid.

2. The process according to claim 1 wherein the compound of formula III, wherein m is 1, is prepared by treating the compound of the formula

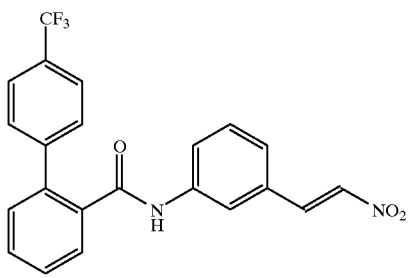
IV in an inert medium, containing a first acid, with a reducing agent selected from hydrogen in the presence of a hydrogenation catalyst, aluminum hydride, borane and borohydride.

3. The process according to claim 2 wherein the compound of the formula IV is prepared by treating the compound of the formula

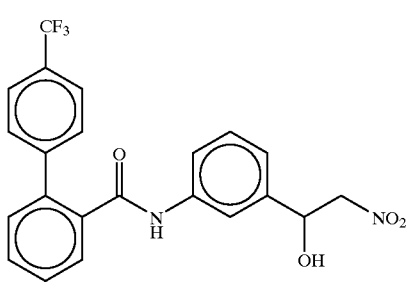
V with a dehydrating agent, which is $(C_1-C_6)$alkyl or $(C_6-C_{10})$aryl sulfonyl or carbonyl halide or anhydride, in the presence of a base.

4. The process according to claim 3 wherein the compound of the formula V is prepared by treating the compound of the formula

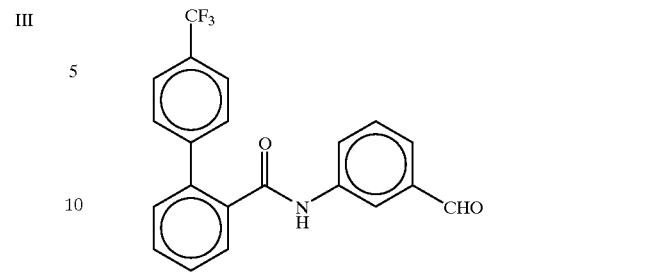
VI with nitromethane in the presence of a base.

5. The process according to claim 4 wherein the compound of the formula VI is prepared by treating the compound of the formula

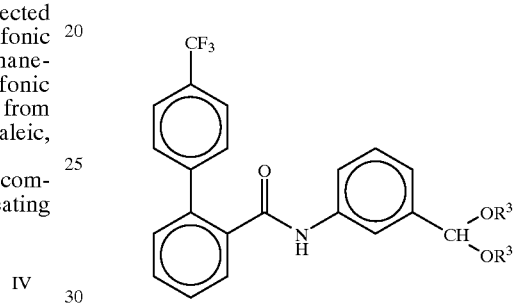
VII wherein each $R^3$ is, independently, selected from $(C_1-C_6)$ alkyl or both $R^3$s together form a group of the formula

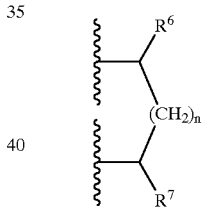

wherein n is 0 or 1 and $R^6$ and $R^7$ are each selected from H and $(C_1-C_2)$alkyl or $R^6$ and $R^7$ together with the carbons to which they are attached form a $(C_3-C_8)$cycloalkyl or $(C_6-C_{10})$aryl ring, with an aqueous acid.

6. The process according to claim 5 wherein the compound of the formula VII is prepared by treating the compound of the formula

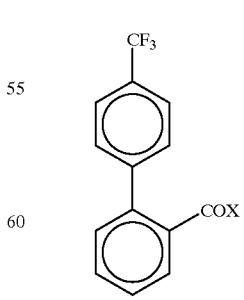
VIII wherein X is a leaving group for acylation of amines, selected from halo, $(C_2-C_6)$acyloxy, $(C_6-C_{10})$aroyloxy, and $(C_6-C_{10})$aryloxy, with a compound of the formula

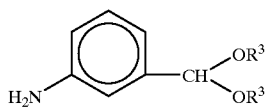

wherein each $R^3$ is as defined in claim 5.

7. The process according to claim 6 wherein the compound of the formula IX is prepared by treating the compound of the formula

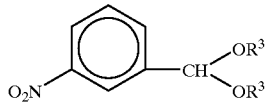

wherein $R^3$ is as described in claim 5, with a reducing agent.

8. The process according to claim 7 wherein the compound of the formula X is prepared by treating the compound of the formula

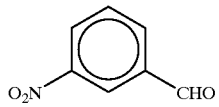

with a compound of the formula $R^3OH$, wherein $R^3$ is $(C_1-C_6)$alkyl, or a compound of the formula

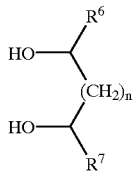

wherein n, $R^6$ and $R^7$ are as defined in claim 5.

9. A compound of the formula

wherein

A is a group of the formula

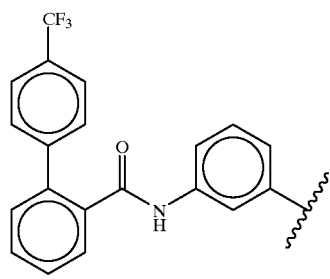

and $R^1$ is selected from H and $OR^3$ wherein $R^3$ is hydrogen or $(C_1-C_6)$alkyl, $R^2$ is selected from $OR^3$, $-CH_2-NH_2\cdot(R^5H)_n$, wherein n is 0 or 1 and $R^5H$ is an acid selected from mineral acids selected from hydrochloric, sulfuric, nitric and phosphoric acid; organic acids selected from sulfonic acids which are selected from benzenesulfonic (besylic), p-toluenesulfonic (PTSA tosylic), methanesulfonic (MSA, mesylic) and trifluoromethanesulfonic (triflic) acid; and carboxylic acids which are selected from formic, acetic, propionic, benzoic, citric, tartaric, maleic, fumaric, succinic and malic acid, or $-CH_2-NO_2$; or $R^1$ and $R^2$ together form an $=O$ or $=CH-NO_2$ group; with the proviso when $R^2$ is $OR^3$, $R^1$ is $OR^3$ and that when $R^1$ and $R^2$ are each an $OR^3$ group then both $R^3$s are $(C_1-C_6)$alkyl groups and are the same; and when $R^2$ is $-CH_2-NH_2$, $(R^5H)_n$, $R^1$ is H; and when $R^2$ is $CH_2NO_2$, $R^1$ is $OR^3$ wherein $R^3$ is hydrogen.

10. A process for preparing the compound of the formula

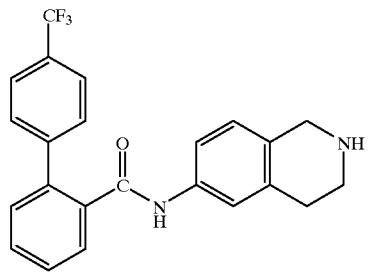

which comprises the steps of a) treating the compound of the formula

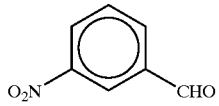

with a compound of the formula $R^3OH$, wherein $R^3$ is $(C_1-C_6)$alkyl, or a compound of the formula

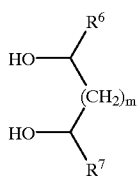

wherein n, $R^6$ and $R^7$ are each selected form H and $(C_1-C_2)$alkyl or $R^6$ and $R^7$ together with the carbons to which they are attached form a $(C_3-C_6)$cycloalkyl or $(C_6-C_{10})$ aryl ring, in the presence of an acid, to form the compound of the formula

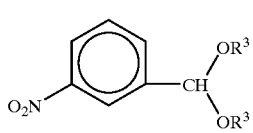

wherein each $R^3$ is, independently, selected from $(C_1-C_6)$alkyl or both $R^3$s together form a the group of the formula

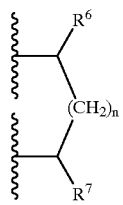

wherein n, $R^6$ and $R^7$ are as described above;

b) treating the compound of the formula X with a reducing agent to form the compound of the formula

IX

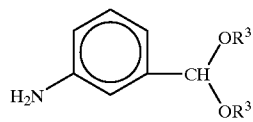

c) treating the compound of the formula IX with the the compound of the formula

VIII

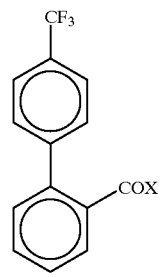

wherein X is a leaving group for the acylation of amines, to form the compound of the formula

VII

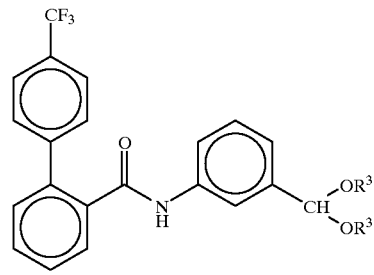

wherein $R^3$ is as described above;

d) treating the compound of the formula VII with an aqueous acid to form the compound of the formula

VI

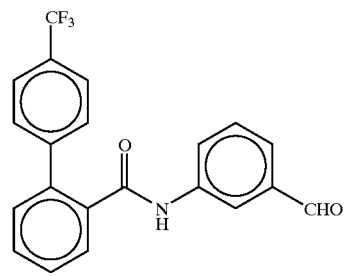

e) treating the compound of the formula VI with nitromethane in the presence of a base, to form the the compound of the formula

V

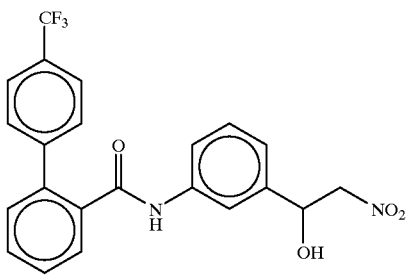

f) treating the compound of the formula V with a dehydrating agent, which is $(C_1-C_6)$alkyl or $(C_6-C_{10})$aryl sulfonyl or carbonyl halide or anhydride, in the presence of a base to form the compound of the formula

IV

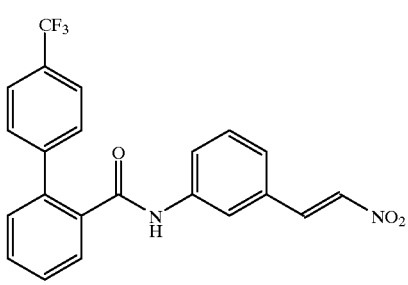

g) treating the compound of the formula IV in an inert medium, containing a first acid, with a reducing agent selected from aluminum hydride, borane, borohydride, and hydrogen in the presence of a hydrogenation catalyst to form the compound of the formula

III

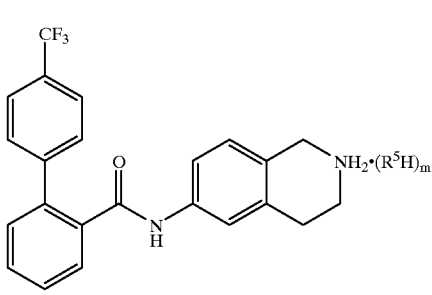

wherein m is 1 and $R^5H$ is selected from mineral acids which are selected from hydrochloric, sulfuric, nitric and phosphoric acid; organic acids selected from sulfonic acids which are selected from benzenesulfonic (besylic), p-toluenesulfonic (PTSA, tosylic), methanesulfonic (MSA, mesylic) and trifluoromethanesulfonic (triflic) acid; and carboxylic acids which are selected from formic, acetic, proprionic, benzoic, citric, tartaric, maleic, fumaric, succinic and malic acid; and optionally neutralizing the $R^5H$ to form the the compound of the formula III wherein m is 0; and h) treating the compound of the formula III, with a source of formaldehyde in the presence of a second acid.

* * * * *